United States Patent
Tsai

(10) Patent No.: US 7,276,600 B2
(45) Date of Patent: *Oct. 2, 2007

(54) PHTHALOCYANINE DERIVATIVES AND THEIR APPLICATIONS IN OPTICAL RECORDING MEDIA

(76) Inventor: Yen Cheng Tsai, 12F., No. 69, Sec. 2, Chenggong Rd., Yonghe City, Taipei County 23453 (TW)

( * ) Notice: Subject to any disclaimer, the term of this patent is extended or adjusted under 35 U.S.C. 154(b) by 0 days.

This patent is subject to a terminal disclaimer.

(21) Appl. No.: 11/149,252

(22) Filed: Jun. 10, 2005

(65) Prior Publication Data

US 2006/0281026 A1    Dec. 14, 2006

(51) Int. Cl.
 *C07F 17/00* (2006.01)
 *G11B 7/24* (2006.01)
(52) U.S. Cl. ............... 540/140; 430/270.16; 430/59.4; 430/945
(58) Field of Classification Search ............... 540/140; 430/270.16, 59.4, 945
See application file for complete search history.

(56) References Cited

U.S. PATENT DOCUMENTS

2002/0099204 A1* 7/2002 Wolleb et al. ............. 540/140

* cited by examiner

*Primary Examiner*—Johann R. Richter
*Assistant Examiner*—Paul V. Ward
(74) *Attorney, Agent, or Firm*—Rabin & Berdo, P.C.

(57) ABSTRACT

An optical recording medium is disclosed, which is composed of a substrate, a recording layer comprising an organic dye upon which information can be recorded by a laser beam, a reflective layer and a protective layer formed in such order; whereas the aforementioned organic dye is a substituted phthalocyanine compound chemically bonded to substituted or un-substituted ferrocene via an anhydride group and a bridge unit G, wherein said G is selected from —O—, —S—, —S—$(CH_2)_{1-6}$—, —(NH)—, —N(alkyl)—, —$(CH_2)$—, —CH(alkyl)—, —C(alkyl)$_2$—, —$(CH_2$—O)—, —C(=O)—, —C—O—C(=O)—, —O—C(=O)—, and —C(=O)—O—.

6 Claims, No Drawings

PHTHALOCYANINE DERIVATIVES AND THEIR APPLICATIONS IN OPTICAL RECORDING MEDIA

BACKGROUND OF THE INVENTION

1. Field of the Invention

This invention relates to a class of novel organic optical dyes of phthalocyanine derivatives and their applications in optical recording media, primarily to the use in recordable compact disc (CD-R).

2. Description of the Prior Art

Organic dyes have been widely employed in the field of optical recording of information. These recording media, which can only be recorded once but repeatedly played back, are therefore abbreviated as "WORM" (write once read many). Recordable compact discs, or the so-called CD-R, as the first example in disc format utilizing this technology, are known from "Optical Data Storage 1989," Technical Digest Series, vol. 1, 45 (1989).

Among all the organic dyes for optical recording media, phthalocyanine derivatives are one of the most important categories, due largely to its high absorption in the near IR range (700~900 nm). Compared to other organic dyes such as cyanines, phthalocyanine dyes exhibit better light-fastness and resistance to temperature and humidity.

Earlier literatures such as JP-A 154888 (1986), 197280 (1986), 246091 (1986), U.S. Pat. No. 4769307 (1987) and JP-A 39388 (1988) described phthalocyanines as a component material in the recording layer of an optical recording medium. However, in terms of sensitivity, solubility, reflectivity, recording performance and other related properties, the above-described phthalocyanines could not be considered as appropriate materials for an optical recording medium.

In order to improve the aforementioned disadvantages associated with the use of phthalocyanine as an optical recording material, JP-A 62878 (1991) provided phthalocyanines with bulkier (greater steric hindrance) substituents on its phenyl rings. These materials, however, did not meet the recording requirements. In U.S. Pat. No. 5,229,507 (1993), phenyl-substituted phthalocyanines (also called naphthalocyanines) were proposed but the dyes exhibited insufficient solubility. Under certain process conditions, dyes would precipitate in the course of spin coating.

Solubility issue was further addressed in U.S. Pat. No. 5,641,879 (1997) by introducing various bulkier substituents onto the phenyl rings of phthalocyanine. However, inadequate reflective index was found. Isomer effects on solubility were studied in U.S. Pat. No. 5,663,326 (1997). It was reported that composition of the two isomers having one pair of alkoxy substituents heading toward each other needed to be greater than 80% in order to obtain desired solubility. It is obviously tedious for dye manufacturing processes and seemingly impractical to assure the isomer composition for quality control.

Another approach to address solubility issue was taken in U.S. Pat. No. 5,820,962 (1998) by introducing substituted trivalent metal as the central atom of phthalocyanine. Due to the bulkiness of the proposed structure, the compound dissolved well in polar solvents and the resulting discs showed good reflectivity. However, polar solvent inherited the hydrophilic character and inevitably led to the difficulties in absorbing moistures during recycling. Consequently, it resulted in quality inconsistency and even deterioration of the disc performances.

In addition to solubility, dye sensitivity is another critical factor for recording media, particularly to enable high-speed recording and fast access to the recorded information. Addition of the so-called "pit edge control agent" was proposed in U.S. Pat. No. 5,492,744 (1996) and JP-A-798887 to improve deviation and jitter properties. Ferrocenes and its derivatives (e.g. benzoylferrocene and n-butylferrocene) blended with substituted phthalocyanine at certain ratios were suggested. Pit formations were reported to be largely improved but material utilization had become an issue in the real-life practices. Since optical dyes account for considerable ratio in recordable disc cost structure, dyes (and dye solutions) have been designed and synthesized to be recycled. Phthalocyanine exhibits better solubility in the designated solvent (ethylcyclohexane, in this case) than ferrocene does. Consequently, the blended-in pit edge control agent tends to precipitate out during spin coating and recycling, resulting in the undesired concentration changes in the recycled dye solutions. The yield (productivity) is therefore inferior to those with single dyes. A minor modification was seen in U.S. Pat. No. 5,789,138 (1998), in which phthalocyanine was blended with (or dissolved in) melted additive (e.g. benzimidazole) so that coordination occurred from the additive to the center metal of phthalocyanine. The thus-obtained dyestuff would exhibit better intermolecular associations to obtain desired film pattern. However, the trade-off between the limited coordination chemistry and the corresponding dye performance made it difficult to optimize disc performances.

Halogenation on phthalocyanine was also reported to improve sensitivity. U.S. Pat. No. 5,646,273 (1997) claimed OPC (optimal power calibration, or "optimal recording power") was effectively improved by halogenation on the alkyl and/or alkoxy substituents to phthalocyanine. Halogenation directly on the phenyl ring of phthalocyanine, on the other hand, was also proposed in U.S. Pat. No. 6,087,492 (2000). However, these resulting discs still showed insufficient sensitivity and unsatisfactory controls in the formation of information pits. Nevertheless, precise reaction control in the degree of halogenation was difficult. The resulting compound was inevitably a mixture containing various numbers of halogen atoms, leading to unstable dye quality and inconsistent disc properties.

In U.S. Pat. No. 6,087,492 (2000), substituted phthalocyanine with divalent metal as the central atom was formylated, further reduced, followed by esterification. Without pit edge control agent in the structure or blended in the formula as described in U.S. Pat. No. 5,492,744 (1996), the resulting dye did not render satisfactory properties. Improvement was made in U.S. Pat. No. 6,399,768 B1 (2002) and U.S. Pat. No. 6,790,593 B2 (2004) by chemically bonding ferrocene to phthalocyanine through ester linkage. These metallocenyl phthalocyanines were halogenated (mainly brominated) at various degrees, depending on the central metal atoms. It was claimed that the resulting dyes exhibited good optical sensitivity and solubility to solvents such as di-butyl ether (DBE) and ethylcyclohexane (ECH). Although these dyes demonstrated satisfactory recording properties at high recording speeds, it did not show equally good performances at low recording rates. Particularly at 1× recording, the discs presented imprecise pit lengths and accordingly, less-than-satisfactory deviation properties.

To address the aforementioned disadvantages derived from the conventional techniques, this invention provides novel optical dyes with unique chemical linkages between the substituted or unsubsituted ferrocenes and phthalocyanine derivatives. Discs made of these novel optical dyes show excellent performances at 1× through 52× recordings.

SUMMARY OF THE INVENTION

One of the major objects of this invention is to provide novel optical dyes composed of a ferrocenyl group chemically bonded to a phthalocyanine through a moiety containing an anhydride group, and could be represented by the following formula (1):

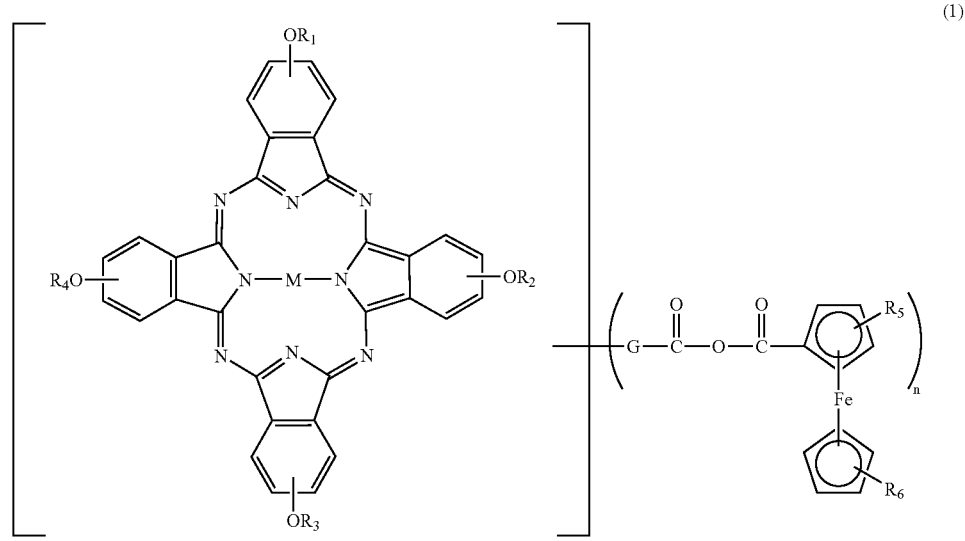

(1)

wherein $R_1$, $R_2$, $R_3$, and $R_4$ each independently represents an alkyl group containing 1 to 12 carbon atoms and with substituents selected from the groups consisting of 0 to 6 halogen atoms, a hydroxyl, an alkoxy group containing 1 to 6 carbon atoms, an alkylamino group containing 1 to 6 carbon atoms, a dialkylamino group containing 1 to 6 carbon atoms, and an alkylthio group containing 1 to 6 carbon atoms; an alkenyl group containing 2 to 12 carbon atoms; or an alkynyl group containing 2 to 12 carbon atoms; M may be two hydrogen atoms, a divalent metal, a monosubstituted trivalent metal, a disubstituted tetravalent metal, or an oxometal group; G represents the linkage between said phthalocyanine and said anhydride group, and is selected from the groups consisting of —O—, —S—, —S—$(CH_2)_{1-6}$—, —(NH)—, —N(alkyl)—, —($CH_2$)—, —CH(alkyl)—, —C(alkyl)$_2$—, —($CH_2$—O)—, —C(=O)—, —C—O—C(=O)—, —O—C(=O)— and —C(=O)—O—; $R_5$ and $R_6$ each independently represent hydrogen, halogen (i.e., fluorine, chlorine, bromine, or iodine), an alkyl group containing 1 to 6 carbon atoms, an alkoxy group containing 1 to 6 carbon atoms, an alkylamino group containing 1 to 6 carbon atoms, an alkylthio group containing 1 to 6 carbon atoms, an alkenyl group containing 1 to 6 carbon atoms, an alkynyl group containing 1 to 6 carbon atoms, or an aromatic substituent; and n is an integer of 1 to 4.

Another object of this invention is to provide the use of said organic dyes according to formula (1) as the optical dyes in the recording layer of a recordable disc to impart the recordable discs excellent recording properties.

Yet another object of the invention is to provide an optical recording medium using said novel phthalocyanine derivatives according to formula (1) as the optical dyes in the recording layer thereof.

DETAILED DESCRIPTION OF THE PREFERRED EMBODIMENT

As described previously, this invention provides phthalocyanine derivatives as optical dyes to be used in the recording layer of an optical recording medium composed of a pre-grooved substrate, a recording layer upon which information can be recorded by a laser beam, a reflective layer and a protective layer formed in such order. Said optical dye is a phthalocyanine derivative (or mixture of derivatives) whose structures can be represented by following formula (1):

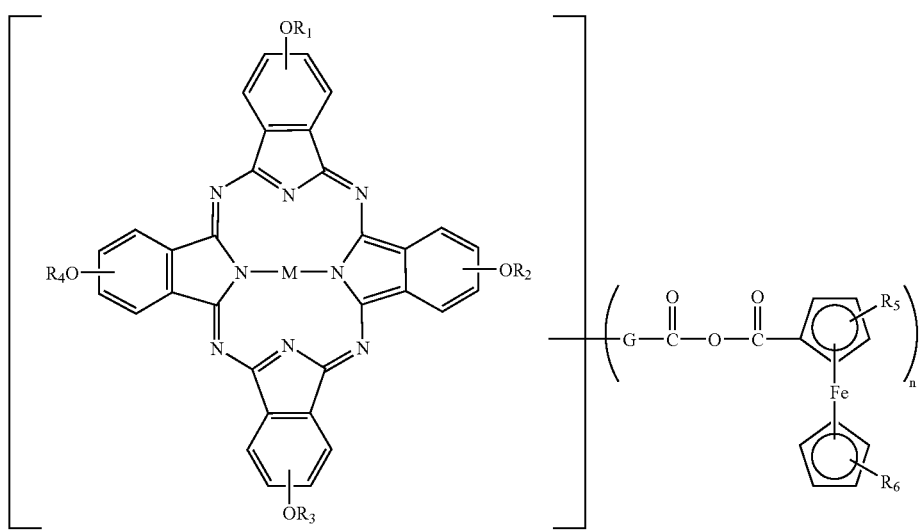

(1)

wherein $R_1$, $R_2$, $R_3$, and $R_4$ each independently represents an alkyl group containing 1 to 12 carbon atoms and with substituents selected from the groups consisting of 0 to 6 halogen atoms, a hydroxyl, an alkoxy group containing 1 to 6 carbon atoms, an alkylamino group containing 1 to 6 carbon atoms, a dialkylamino group containing 1 to 6 carbon atoms, and an alkylthio group containing 1 to 6 carbon atoms; an alkenyl group containing 2 to 12 carbon atoms; or an alkynyl group containing 2 to 12 carbon atoms; M may be two hydrogen atoms, a divalent metal, a monosubstituted trivalent metal, a disubstituted tetravalent metal, or an oxometal group; G represents the linkage between said phthalocyanine and said anhydride group, and is selected from the groups consisting of —O—, —S—, —S—$(CH_2)_{1-6}$—, —(NH)—, —N(alkyl)—, —$(CH_2)$—, —CH(alkyl)—, —C(alkyl)$_2$—, —$(CH_2$—O)—, —C(=O)—, —C—O—C(=O)—, —O—C(=O)— and —C(=O)—O—; $R_5$ and $R_6$ each independently represent hydrogen, halogen (i.e., fluorine, chlorine, bromine, or iodine), an alkyl group containing 1 to 6 carbon atoms, an alkoxy group containing 1 to 6 carbon atoms, an alkylamino group containing 1 to 6 carbon atoms, and an alkylthio group containing 1 to 6 carbon atoms; an alkenyl group containing 2 to 6 carbon atoms; an alkynyl group containing 2 to 6 carbon atoms; or an aromatic substituent; and n is an integer of 1 to 4.

As noted above, the phthalocyanine dye (1) provided by the invention is consisted of a ferrocenyl group chemically linked with phthalocyanine derivative through a moiety containing an anhydride group. The phthalocyanine derivative employed in this invention can be prepared according to a process described in, for example, EP 70328, or it can be obtained from commercial sources. Among those phthalocyanine derivatives, the α-substituted phthalocyanines are most preferred. Those phthalocyanine derivatives used in this invention may comprise several isomers as represented by formulae (2) to (5):

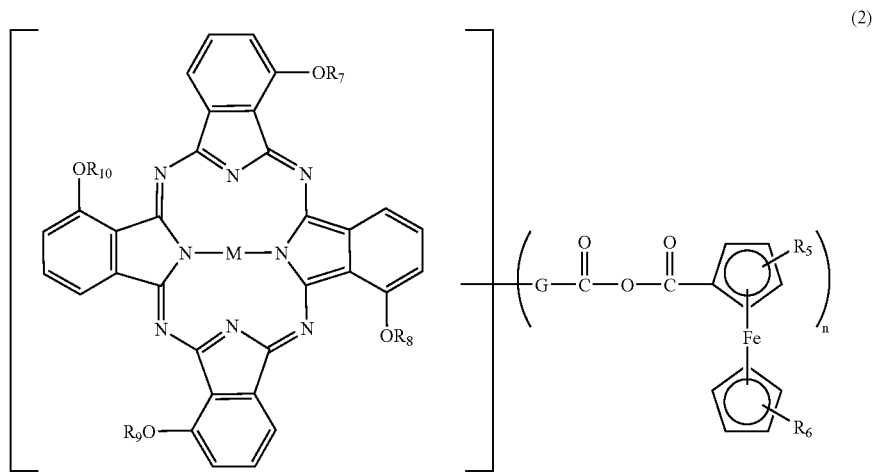

(2)

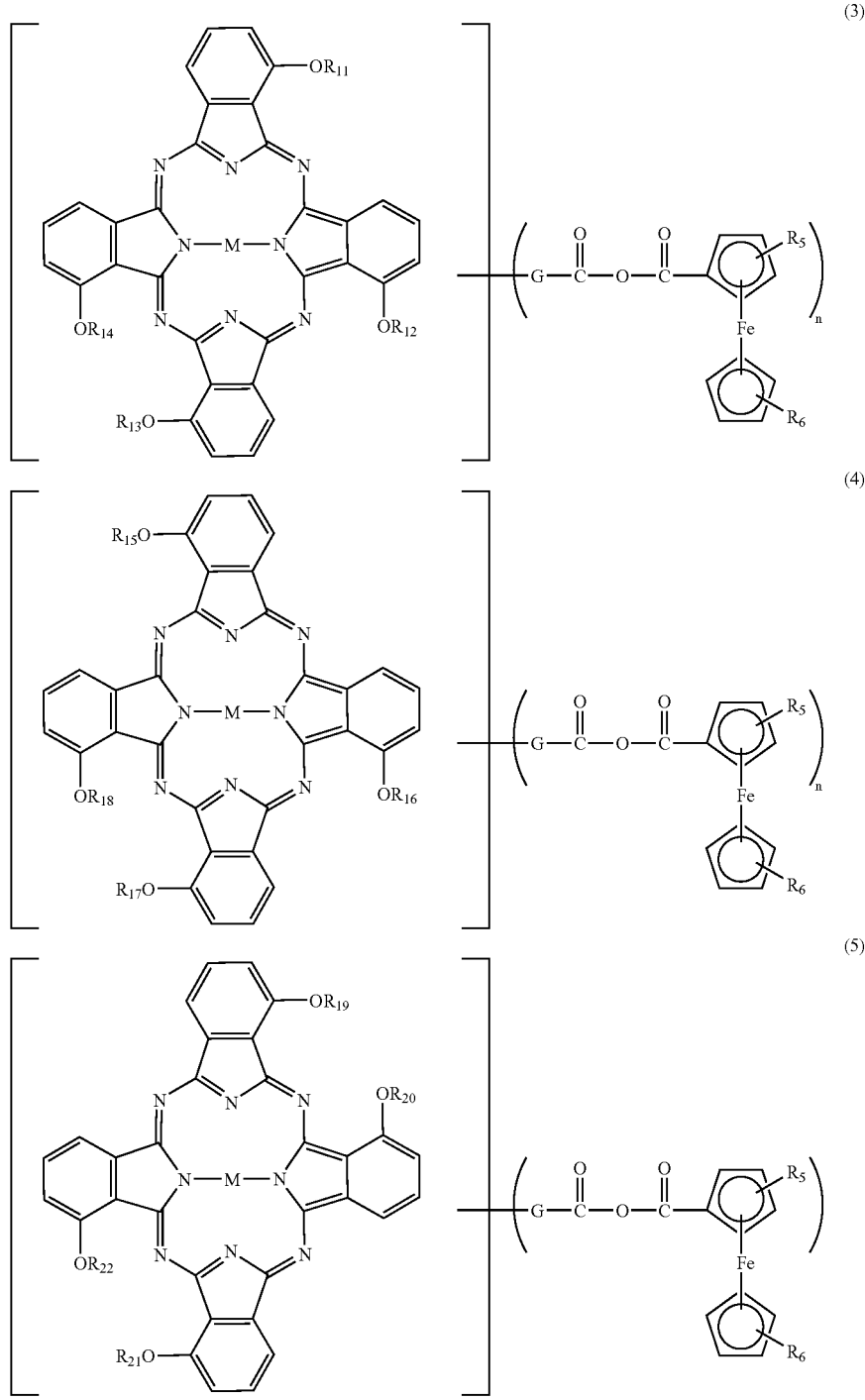

wherein $R_5$, $R_6$ and G are defined as those in formula (1); $R_7$ to $R_{22}$ each independently represents an alkyl group containing 1 to 12 carbon atoms and with substituents selected from the groups consisting of 0 to 6 halogen atoms, a hydroxyl, an alkoxy group containing 1 to 6 carbon atoms, an alkylamino group containing 1 to 6 carbon atoms, a dialkylamino group containing 1 to 6 carbon atoms, and an alkylthio group containing 1 to 6 carbon atoms; an alkenyl group containing 2 to 12 carbon atoms; or an alkynyl group containing 2 to 12 carbon atoms; and M may be two hydrogen atoms, a divalent metal, a monosubstituted trivalent metal, a disubstituted tetravalent metal, or an oxometal group.

The isomeric compositions of the aforementioned four α-substituted phthalocyanines may vary according to reaction conditions and as desired. Preferred substituents therein are secondary alkyl, alkenyl, or alkynyl. The most preferred substituents are alkyl, alkenyl, or alkynyl groups containing 2 to 4 secondary, tertiary, or quaternary carbon atoms.

As $R_1$ to $R_{20}$ in formula (1) to (5), representative alkyl groups are, for example, methyl, ethyl, n-propyl, i-propyl, n-butyl, i-butyl, s-butyl, t-butyl, n-pentyl, i-pentyl, cyclopentyl, 2-methylbutyl, 1,2-dimethylpropyl, n-hexyl, cyclohexyl, 2-methylpentyl, 3-methylpentyl, 4-methylpentyl, 1,2-dimethylbutyl, 1,3-dimethylbutyl, 2,2-dimethylbutyl, 2,3-dimethylbutyl, 3,3-dimethylbutyl, 1-(i-propyl)propyl, n-heptyl, cycloheptyl, 2-methylhexyl, 3-methylhexyl, 4-methylhexyl, 5-methylhexyl, 1,2-dimethylpentyl, 1,3-dimethylpentyl, 1,4-dimethylpentyl, 2,2-dimethylpentyl, 2,3-dimethylpentyl, 2,4-dimethylpentyl, 1-ethyl-3-methylbutyl, 2-(i-propyl)butyl, 2-methyl-1-(i-isopropyl)propyl, n-octyl, cyclooctyl, 2-ethylhexyl, 3-methyl-1-(i-isopropyl)butyl, 2-methyl-1-(i-isopropyl)butyl, 1-t-butyl-2-methylpropyl, n-nonyl, cyclononyl, n-decyl, cyclodecyl, undecyl, dodecyl; preferable substituents are branched alkyl groups with 2 to 4 secondary, tertiary, or quaternary carbon atoms, for example, i-propyl, i-butyl, s-butyl, t-butyl, i-pentyl, 2-methylbutyl, 1,2-dimethylpropyl, 1,3-dimethylbutyl, 1-(i-propyl)propyl, 1,2-dimethylbutyl, 1,4-dimethylpentyl, 2-methyl-1-(i-propyl)propyl, 1-ethyl-3-methylbutyl, 2-ethylhexyl, 3-methyl-1-(i-propyl)butyl, 2-methyl-1-(i-propyl)butyl, 1-t-butyl-2-methylpropyl, 2,4-dimethyl-3-pentyl; most preferable substituents are, for example, 1-t-butyl-2-methylpropyl, 2-methyl-1-isopropylbutyl, 2,4-dimethyl-3-pentyl.

Representative halogenated alkyl groups are, for example, chloromethyl, 1,2-dichloroethyl, 1,2-dibromoethyl, 2,2,2-trifluoroethyl, 2,2,2-trichloroethyl, 2,2,2-tribromoethyl, 1,1,2,2,2-pentachloroethyl, 1,1,1,3,3,3-hexafluoro-2-propyl.

Representative hydroxyalkyl groups are, for example, hydroxymethyl, 2-hydroxyethyl, 1,2-dihydroxyethyl, 3-hydroxypropyl, 2,3-dihydroxypropyl, 3-hydroxybutyl, 4-hydroxybutyl, 3-hydroxypentyl, 4-hydroxypentyl, 5-hydroxypentyl, 2-hydroxyhexyl, 3-hydroxyhexyl, 4-hydroxyhexyl, 5-hydroxyhexyl, 6-hydroxyhexyl, hydroxyheptyl, hydroxyoctyl, hydroxynonyl, hydroxydecyl, hydroxyundecyl, hydroxydodecyl.

Representative alkoxyalkyl groups are, for example, methoxymethyl, methoxyethyl, methoxypropyl, methoxybutyl, methoxypentyl, methoxyhexyl, 3-methoxycycolpentyl, 4-methoxycyclohexyl, ethoxyethyl, ethoxypropyl, ethoxybutyl, ethoxypentyl, ethoxyhexyl, 4-ethoxycyclohexyl, propoxyethyl, propoxypropyl, propoxybutyl, propoxypentyl, propoxyhexyl, butoxyethyl, butoxypropyl, butoxybutyl, 1,2-dimethoxyethyl, 1,2-diethoxyethyl, 1,2-dimethoxypropyl, 2,2-dimethoxypropyl, diethoxybutyl and butoxyhexyl; preferable substituents are alkoxyalkyl groups containing 2 to 10 carbon atoms, for example, methoxymethyl, methoxyethyl, ethoxypropyl, ethoxybutyl, propoxyhexyl, 1,2-dimethoxypropyl, 2,2-dimethoxypropyl, diethoxybutyl and butoxyhexyl; most preferable substituents are alkoxyalkyl groups containing 2 to 6 carbon atoms, for example, methoxymethyl, methoxyethyl, ethoxypropyl, ethoxybutyl.

Representative alkylaminoalkyl groups are, for example, methylaminomethyl, methylaminoethyl, methylaminopropyl, methylaminobutyl, ethylaminoethyl, ethylaminopropyl, ethylaminobutyl, ethylaminopentyl, ethylaminohexyl, ethylaminoheptyl, ethylaminooctyl, propylaminoethyl, propylaminopropyl, propylaminobutyl, propylaminopentyl, propylaminohexyl, i-propylaminoethyl, i-propylaminopropyl, i-propylaminobutyl, i-propylaminopentyl, i-propylaminohexyl, butylaminoethyl, butylaminopropyl, butylaminopentyl, butylaminohexyl; preferable substituents are alkylaminoalkyl groups containing 2 to 8 carbon atoms, for example, methylaminomethyl, methylaminoethyl, ethylaminopropyl, ethylaminobutyl, ethylaminopentyl, ethylaminohexyl, propylaminobutyl, propylaminopentyl; most preferable substituents are, for example, alkylaminoalkyl groups containing 2 to 6 carbon atoms, for example, methylaminomethyl, methylaminoethyl, ethylaminopropyl, ethylaminobutyl.

Representative dialkylaminoalkyl groups are, for example, dimethylaminomethyl, dimethylaminoethyl, dimethylaminopropyl, dimethylaminobutyl, diethylaminoethyl, diethylaminopropyl, diethylaminobutyl, diethylaminopentyl, diethylaminohexyl, diethylaminoheptyl, diethylaminooctyl, dipropylaminoethyl, dipropylaminopropyl, dipropylaminobutyl, dipropylaminopentyl, dipropylaminohexyl, di(i-propyl)aminoethyl, di(i-propyl)aminopropyl, di(i-propyl)aminobutyl, di(i-propyl)aminopentyl, di(i-propyl)aminohexyl; preferable substituents are dialkylaminoalkyl groups containing 2 to 10 carbon atoms, for example, dimethylaminomethyl, dimethylaminoethyl, diethylaminopropyl, diethylaminobutyl, diethylaminopentyl, diethylaminohexyl; most preferable substituents are dialkylaminoalkyl groups containing 2 to 6 carbon atoms, for example, dimethylaminomethyl, dimethylaminoethyl, diethylaminoethyl.

Representative alkylthioalkyl groups are, for example, methylthiomethyl, methylthioethyl, methylthiopropyl, methylthiobutyl, methylthiopentyl, methylthiohexyl, 3-methylthiocycolpentyl, 4-methylthiocyclohexyl, ethylthioethyl, ethylthiopropyl, ethylthiobutyl, ethylthiopentyl, ethylthiohexyl, 4-ethylthiocyclohexyl, propylthiobutyl, propylthiopentyl, propylthiohexyl; preferable substituents are alkylthioalkyl groups containing 2 to 8 carbon atoms, for example, methylthiomethyl, methylthioethyl, ethylthiopropyl, ethylthiobutyl, propylthiohexyl; most preferable substituents are alkylthioalkyl groups containing 2 to 6 carbon atoms, for example, methylthiomethyl, methylthioethyl, ethylthiopropyl, ethylthiobutyl.

Representative alkenyl groups are, for example, ethenyl, n-propenyl, i-propenyl, n-butenyl, i-butenyl, s-butenyl, n-pentenyl, i-pentenyl, cyclopentenyl, 2-methylbutenyl, 1,2-dimethylpropenyl, n-hexenyl, cyclohexenyl, n-heptenyl, cycloheptenyl, n-octenyl, cyclooctenyl, n-nonenyl, cyclononenyl, n-decenyl, cyclodecenyl, undecenyl and dodecenyl; preferable substituents are alkenyl groups containing 2 to 6 carbon atoms, for example, ethenyl, n-propenyl, i-propenyl, n-butenyl, i-butenyl, s-butenyl, n-pentenyl, i-pentenyl, cyclopentenyl, 2-methylbutenyl, 1,2-dimethylpropenyl, n-hexenyl, cyclohexenyl; most preferable substitutents are alkenyl groups containing 2 to 4 carbon atoms, for example, ethenyl, n-propenyl, i-propenyl, n-butenyl, i-butenyl, s-butenyl, t-butenyl.

Representative alkynyl groups are, for example, ethynyl, propynyl, n-butynyl, s-butynyl, n-pentynyl, i-pentynyl, cyclopentynyl, 2-methylbutynyl, n-hexynyl, cyclohexynyl, n-heptynyl, cycloheptynyl, n-octynyl, cyclooctynyl, n-nonynyl, cyclononynyl, n-decynyl, cyclodecynyl, undecynyl, dodecynyl; preferable substituents are alkynyl groups containing 2 to 6 carbon atoms, for example, ethynyl, propynyl, n-butynyl, s-butynyl, n-pentynyl, i-pentynyl, cyclopentynyl, 2-methylbutynyl, n-hexynyl, cyclohexynyl; most preferable substituents are alkynyl groups containing 2 to 4 carbon atoms, for example, ethynyl, propynyl, n-butynyl, s-butynyl.

The representative divalent central metal M in formula (1) to (5) may be, for example, copper, zinc, iron, cobalt, nickel, palladium, platinum, manganese, tin, ruthenium, osmium; most preferred metals are copper, cobalt, nickel, palladium, platinum. The representative monosubstituted trivalent metals are, for example, fluorine-aluminum, chlorine-aluminum, bromine-aluminum, iodine-aluminum, fluorine-indium, chlorine-indium, bromine-indium, iodine-indium, fluorogallium, chlorogallium, bromogallium, iodogallium, fluorothallium, chlorothallium, bromothallium, iodothallium, hydroxyaluminum, hydroxymanganese. The representative disubstituted tetravalent metals are, for example, difluorosilicon, dichlorosilicon, dibromosilicon, diiodosilicon, difluorotin, dichlorotin, dibromotin, diiodotin, difluorogermanium, dichlorogermanium, dibromogermanium, diiodogermanium, difluorotitanium, dichlorotitanium, dibromotitanium, diiodotitanium, dihydroxysilicon, dihydroxytin, dihydroxygermanium, dihydroxymanganese. The representative oxometal groups are, for example, oxovanadium, oxomanganese, oxotitanium.

In order to improve the performances of phthalocyanine during recording, according to this invention, a substituted or un-substituted ferrocene group is covalently bonded to a phthalocyanine derivative through a moiety containing an anhydride group. Not only can the thus-obtained dye meet the requirements for 1× to 52× recordings on various writers, but it also enables the precise controls in pit formations. This in turn largely improves the pit deviation properties.

Synthetic pathways utilized to chemically link a substituted or un-substituted ferrocenyl compound to a phthalocyanine derivative through anhydride moiety are many, including direct reaction of ferrocene carboxylic acid with a phthalocyanine substituted with acyl chloride, or acyloxylation of aldehyde-substituted phthalocyanine and perester of ferrocene carboxylate with a metal catalyst, or a hydroxyl-substituted phthalocyanine reacting, in the presence of a suitable catalyst (e.g. pyridine), with an intermediate which is obtained by treating ferrocene carboxylic acid with a third reactant (e.g. oxalic acid or oxalyl chloride).

Another preferred embodiment of this invention relates to an optical recording medium composed of a substrate, a recording layer, a reflective layer and a protective layer formed in such order, wherein said recording layer comprises the above-described phthalocyanine derivative (1) provided by this invention as the optical dye.

In said optical recording medium provided by this invention, the substrate is generally made of a transparent optical resin, such as, for example, acrylic, polyethylene, polystyrene or polycarbonate resins. Meanwhile, the surface of the substrate can be treated with a thermosetting resin or UV cross-linkable resin, if necessary.

The recording layer can be formed by spin coating a solution of the phthalocyanine derivative (1) provided by this invention onto the substrate. The spin coating process can be carried out as follows: dissolving the phthalocyanine derivative of this invention in a solvent at an appropriate ratio, desirably no more than 5% wt/vol (weight/volume ratio), and preferably, 1.5-3%. Subsequently, the resulting solution can be applied onto the substrate via conventional spin coating technique. The thickness of a recording layer is generally between 50 and 300 nm, and preferably, between 80 and 150 nm.

Taking into account the solubility of organic optical dye in a specific solvent and the possible erosion toward substrate by the solvent, a preferred solvent for spin coating could be selected from halogenated hydrocarbons, for example, dichloromethane, chloroform, carbon tetrachloride, trichloroethane, dichloroethane, tetrachloroethane and dichlorodifluoroethane; ethers, for example, ethyl ether, propyl ether, butyl ether and cyclohexyl ether; alcohols, for example, methanol, ethanol, propanol, tetrafluoropropanol and butanol; ketones, for example, acetone, trifluoroacetone, hexafluoroacetone and cyclohexanone; and hydrocarbons, for example, hexane, cyclohexane, methylcyclohexane, dimethylcyclohexane, octane and cyclooctane.

The reflective layer is composed mainly of metals such as copper, aluminum, gold or silver, or alloy thereof. The reflective layer can be formed by depositing suitable material(s) upon the recording layer through vacuum deposition or sputtering at a thickness between 1 and 200 nm.

The protective layer is composed mostly of a thermosetting resin or a UV cross-linkable resin, and preferably a transparent resin. In common practice, the protective layer can be formed by spin coating the resin onto the reflective layer to form a layer with thickness between 0.1 and 500 micrometer, and preferably, between 0.5 and 50 micrometer.

From the practicality viewpoint, polycarbonate resin is nowadays predominantly employed as the substrate material of the optical recording medium while spin coating process is the primary choice for forming the recording and protective layers.

The prime spirit of this invention can be best illustrated, but not limited to, in further details by the following examples. Any directly or indirectly related derivatives based upon the prime spirit of this invention will be considered to fall within the scope of this invention.

EXAMPLES

Example 1

10.0 g tetra-α-(2,4-dimethyl-3-pentoxyl) copper phthalocyanine derivative (prepared according to EP 703280) was weighed into a 250 ml round-bottom flask with nitrogen purge. 50 ml toluene and 5.4 g N-methylformamide were then added thereto. After complete dissolution, the temperature of the resulting solution was lowered to 0° C. Once the temperature was stabilized, 5.6 g $POCl_3$ was slowly added into the reaction solution, while keeping the temperature not exceeding 5° C. The cooling system was removed after the complete addition of $POCl_3$ and the temperature was further raised to 50° C. The reaction solution was stirred at 50° C. for 24 hours. Reaction was monitored with thin layer chromatography (TLC) till completion. The reaction mixture was then poured into iced 200 ml sodium acetate (41.5 g) solution and stirred for 30 minutes, followed by extraction with 100 ml×3 toluene. The combined organic layers were dried over 20 g anhydrous magnesium sulfate which was later filtered off, followed by concentrating under reduced pressure to about 60 ml. The concentrate was poured into 1 L mixed solvent of methanol/water (98/2), vigorously stirred for 30 minutes. Product was collected by filtration, followed by washing with 1 L methanol, and dried in a vacuum oven at 70° C. for two days. The thus-obtained green powder was 9.5 g (64% theory).

Elemental analysis: Found (%): C, 69.21; H, 6.79; N, 10.44; Calculated (%): C, 69.06; H, 6.84; N, 10.56;

UV-VIS(DBE): λ max=710 nm

IR (KBr): C=O absorption at 1675 $cm^{-1}$.

Example 2

1.03 g sodium borohydride was weighed into a 250 ml three-necked round-bottom flask with nitrogen purge, followed by addition of 40 ml ethanol to dissolve the sodium borohydride. 10.0 g formylated tetra-α-(2,4-dimethyl-3-pentoxyl) copper phthalocyanine derivative (prepared as in Example 1) was dissolved in 40 ml tetrahydrofuran (THF), and then added into the reducing agent solution prepared above. The resulting reaction solution was stirred vigorously at ambient temperature for 24 hours and was monitored with thin layer chromatography (TLC). At the end of the reaction, the insoluble was filtered off and the reaction was terminated by pouring 200 ml 20% saline solution thereto. The mixture was then extracted with 40 ml×3 toluene. The combined organic layers were dried over 20 g anhydrous magnesium sulfate which was later filtered off, followed by concentrating under reduced pressure to about 40 ml. The thus-obtained concentrate was poured into 1 L mixed solvent of methanol/water (98/2), stirred vigorously for 30 minutes. Product was collected by filtration, followed by washing with 1 L methanol, and dried in a vacuum oven at 70° C. for two days. The thus-obtained green powder was 9.4 g (95% theory).

Elemental analysis: Found (%): C, 68.77; H, 7.20; N, 10.56; Calculated (%): C, 68.93; H, 7.02; N, 10.54.

UV-VIS (DBE): λ max=713.5 nm.

IR (KBr): C=O absorption at 1675 $cm^{-1}$ disappeared, and OH absorption appeared at 3210 $cm^{-1}$.

Example 3

In a 500 ml reaction flask equipped with nitrogen purge, 4.18 g ferrocene-carboxylicacid and 20 ml dichloromethane was added. At a temperature of 0-5° C., 2.43 g of oxalyl chloride was slowly added therein. After one hour, excess (or unreacted) oxalyl chloride was removed under reduced pressure. 25 ml pyridine was then added while keeping the reaction temperature below 15° C. In addition, a solution containing 10 g compound obtained in Example 2 and 22.5 ml of dichloromethane was separately prepared and was then added into the previous 500 ml reaction flask to react for 3 hours therein. The reaction was terminated by pouring the reaction mixture into a mixed solvent of methanol/water (75/25). Green powder was collected by filtration, followed by vacuum dry at 70° C. for two days to yield 9.7 g (78% theory) product.

UV-VIS (DBE): λ max=712 nm

IR(KBr): 1715, 1743, 1770 $cm^{-1}$.

TGA: Main decomposition (~34%) began around 280° C.

Example 4

A dye solution was so prepared that compound of Example 3 was dissolved in a mixed solvent of dibutyl ether (DBE) and 2,6-dimethyl-4-heptanone (95/5, vol/vol) to form a 2.8% wt/vol (weight percent of solute/solvent volume) dye solution. After vigorously stirred for 1 hour, the solution was first filtered through a Teflon filter of 0.2 micrometer pore size and then spin-coated onto a 1.2 mm-thick pre-grooved disc (average groove depth=195 nm, average groove width =600 nm, and track pitch=1.7 micrometer) at an initial rotation speed of 400 rpm. The rotation was further raised to 3000 rpm to remove excess solution. The thus-formed homogeneous recording layer was dried in circulating hot air at 60° C. for 15 minutes. Subsequently, a 60 nm-thick silver reflective layer was sputtered upon the recording layer in a vacuum sputtering apparatus (ALCATEL, ATP 150). Lastly, a UV hardener (ROHM AND HAAS DEUTSCHLAND GMBH, Rengolux 3203-031v6 clear-CD LACQUER) was spin-coated over the silver reflective layer and further subject to UV curing to form a protective layer with a thickness of 5 mm. Information was recorded successively over the thus-produced blank CD-R disc at 52× recording speed on a commercial writer (Liteon LTR-52327S). The recorded disc was then tested with an automatic compact disc testing system (Pulstec OMT-2000x4) to measure the signals at 1×. Major data at 40-minute position were compiled in Table (1).

Example 5

The procedures described in Example 4 were repeated. Information was recorded successively over the thus-produced blank CD-R disc at 52× recording speed on a commercial writer (Liteon LTR-52327S). The recorded disc was then tested with an automatic compact disc testing system (Pulstec OMT-2000x4) to measure the signals at 1×. Major data at 75-minute position were compiled in Table (1).

TABLE (1)

| Position | BLER | JitP3T | JitP11T | Dev. P3T | Dev. P11T |
| --- | --- | --- | --- | --- | --- |
| 40 min | 2.0 | 25 | 27 | 35 | 14 |
| 75 min | 3.1 | 28 | 31 | −38 | −38 |

(A) BLER: Block Error Rate
(B) JitP3T: Jitter Pit 3T (in ns)
(C) JitP11T: Jitter Pit 11T (in ns)
(D) Dev. P3T: Deviation pit 3T (in ns)
(E) Dev. P11T: Deviation pit 11T (in ns)

Example 6

A dye solution was so prepared that compound of Example 3 was dissolved in a mixed solvent of dimethyl cyclohexane and o-xylene (94:6) to form a 1.7% wt/vol (weight percent of solute/solvent volume) dye solution. After vigorously stirred for 1 hour, the solution was first filtered through a Teflon filter of 0.2 micrometer pore size and then spin-coated onto a 1.2 mm-thick pre-grooved disc (average groove depth=195 nm, average groove width=600 nm, and track pitch=1.7 micrometer) at an initial rotation speed of 400 rpm. The rotation was further raised to 3000 rpm to remove excess solution. The thus-formed homogeneous recording layer was dried in circulating hot air at 60° C. for 15 minutes. Subsequently, a 60 nm-thick silver reflective layer was sputtered upon the recording layer in a vacuum sputtering apparatus (ALCATEL, ATP150). Lastly, a UV hardener (ROHM AND HAAS DEUTSCHLAND GMBH, Rengolux 3203-031v6 clear-CD LACQUER) was spin-coated over the silver reflective layer and further subject to UV curing to form a protective layer with a thickness of 5 mm. Information was recorded successively over the thus-produced blank CD-R disc at 52× recording speed on a commercial writer (BenQ CD-RW 5232X). The recorded disc was then tested with an automatic compact disc testing system (Pulstec OMT-2000x4) to measure the signals at 1×. Major data at 40-minute position were compiled in Table (2).

Example 7

The procedures described in Example 6 were repeated. Information was recorded successively over the thus-produced blank CD-R disc at 52× recording speed on a commercial recorder (Liteon LTR-52327S). The recorded disc was then tested with an automatic compact disc testing system (Pulstec OMT-2000x4) to measure the signals at 1×. Major data at 75-minute position were compiled in Table (2).

TABLE (2)

| Position | BLER | JitP3T | JitP11T | Dev. P3T | Dev. P11T |
|---|---|---|---|---|---|
| 40 min | 2.0 | 26 | 28 | 33 | 18 |
| 75 min | 3.1 | 27 | 27 | −32 | −33 |

As the data shown in Tables (1) and (2), it is evident that the optical recording medium utilizing the invented phthalocyanine dye can all achieve good jitter and deviation performances at different recording speeds on various commercial writers. In addition, the performances of the recorded discs meet the specifications as defined in the Orange Book.

What is claimed is:

1. An optical recording material, with structure represented by formula (I), comprising of a phthalocyanine derivative, to which at least a substituted or unsubstituted metallocene is attached via the linkage containing an anhydride moiety and a bridge unit G:

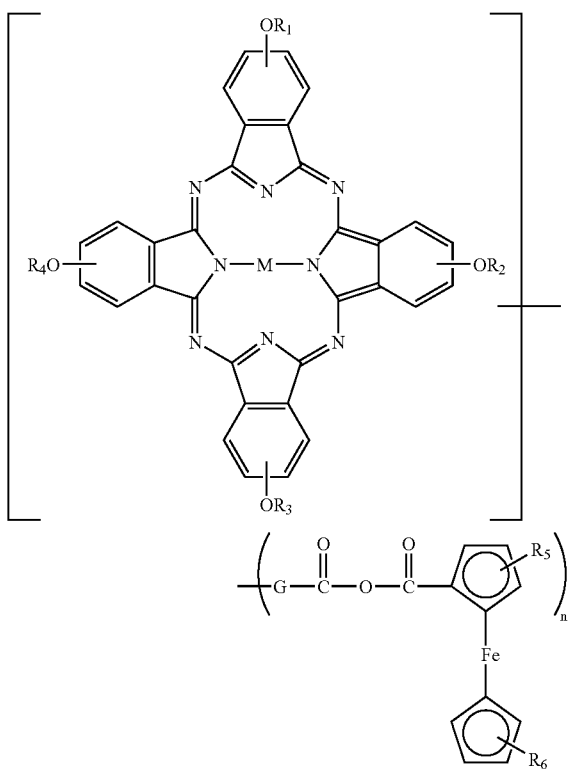

(I)

wherein $R_1$, $R_2$, $R_3$, and $R_4$ are each independently an alkyl group containing 1 to 12 carbon atoms and with substituents selected from the groups consisting of 0 to 6 halogen atoms, a hydroxyl, an alkoxy group containing 1 to 6 carbon atoms, an alkylamino group containing 1 to 6 carbon atoms, a dialkylamino group containing 1 to 6 carbon atoms, and an alkythio group containing 1 to 6 carbon atoms; an alkenyl group containing 2 to 12 carbon atoms; or an alkynyl group containing 2 to 12 carbon atoms;

M is two hydrogen atoms, a divalent metal, a monosubstituted trivalent metal, a disubstituted tetravalent metal, or an oxometal group;

G is the bridge unit between said phthalocyanine derivative and said anhydride moiety connecting metallocene group, and is selected from the groups consisting of —O—, —S—, —S—(CH$_2$)$_{1-6}$—, —(NH)—, —N(alkyl)—, —(CH$_2$)—, —CH(alkyl)—, —C(alkyl)$_2$—, —CH$_2$—O—, —C(=O)—, —C—O—C(=O)—, —O—C(=O)— and —C(=O)—O—;

$R_5$ and $R_6$ are each independently a hydrogen, halogen selected from the group consisting of, an alkyl group containing 1 to 6 carbon atoms, an alkoxy group containing 1 to 6 carbon atoms, an alkylamino group containing 1 to 6 carbon atoms, an alkylthio group containing 1 to 6 carbon atoms, an alkenyl group containing 1 to 6 carbon atoms, an alkynyl group containing 1 to 6 carbon atoms, or an aromatic substituent; and n is a rational number of 1 to 4.

2. An optical recording medium comprising the optical recording material recited in claim 1.

3. The optical recording medium of claim 2, further comprising a substrate, a recording layer, a reflective layer, and protective layer, wherein the optical recording material is placed in the recording layer.

4. An optical recording material according to claim 1, wherein the bridge unit G is —CH$_2$—O—(CO)— and the entire structure is represented by formula (6)

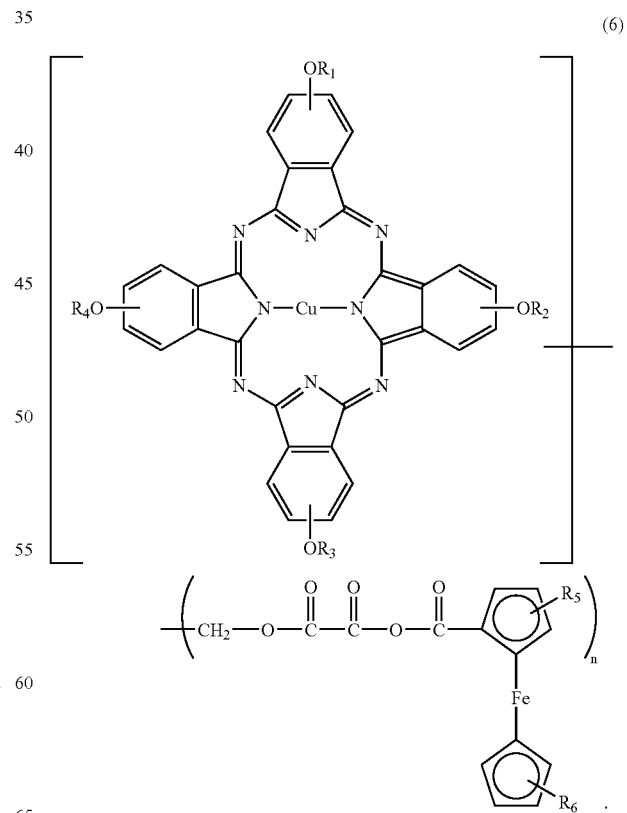

(6)

.

5. An optical recording medium comprising the optical recording material recited in claim 4.

6. The optical recording medium of claim 5, further comprising a substrate, a recording layer, a reflective layer, and protective layer, wherein the optical recording material is placed in the recording layer.

* * * * *